(12) United States Patent
Hung

(10) Patent No.: US 6,852,295 B2
(45) Date of Patent: Feb. 8, 2005

(54) APPARATUS FOR STERILIZING AND SPROUTING GRAINS

(76) Inventor: Chien-Lung Hung, 7/F-1, No. 192, Chienkuo N. Rd., Sec. 2, Taipei City (TW)

( * ) Notice: Subject to any disclaimer, the term of this patent is extended or adjusted under 35 U.S.C. 154(b) by 522 days.

(21) Appl. No.: 10/045,140

(22) Filed: Jan. 15, 2002

(65) Prior Publication Data

US 2003/0133852 A1 Jul. 17, 2003

(51) Int. Cl.[7] ............................................. A23B 9/00
(52) U.S. Cl. ............... 422/292; 422/186.7; 422/186.03; 422/300; 426/442; 426/320; 99/485; 99/516
(58) Field of Search ..................... 422/292, 300, 422/186.3, 186.07; 426/320, 248, 331, 335, 442; 99/485, 516; 47/14, 65.5

(56) References Cited

U.S. PATENT DOCUMENTS 6,120,822 A * 9/2000 Denvir et al. ............... 426/320

6,363,656 B1 * 4/2002 Byun .............................. 47/61

* cited by examiner

Primary Examiner—Robert J. Warden, Sr.
Assistant Examiner—Sean E. Conley
(74) Attorney, Agent, or Firm—Rosenberg, Klein & Lee

(57) ABSTRACT

An apparatus for sterilizing and sprouting grains is constructed to include a container having a water inlet pipe, a water drain pipe, an overflow pipe, and a grains discharge control valve, a top cover covering the container and provided with ultraviolet lamps for sterilizing water in the container, a water supply coil connected to the water inlet pipe for guiding fresh water to the inside of the container, a disk-like wire gauze filter mounted in the container for carrying grains above the water supply coil, active carbon blocks mounted in the space between the water supply coil and the bowl-like wire gauze filter, a temperature sensor adapted to control the temperature of water in the container, an ozone supply pipe adapted to supply ozone to water delivered to the inside of the container, and an ultrasonic generator adapted to generate ultrasonic waves in water in the container.

7 Claims, 3 Drawing Sheets

APPARATUS FOR STERILIZING AND SPROUTING GRAINS

BACKGROUND OF THE INVENTION

1. Field of the Invention

The present invention relates to an apparatus for sterilizing and sprouting grains and, more particularly to a grain sterilizing and sprouting apparatus, which is easy to operate.

2. Description of the Related Art

When sprouting grains, prepared grains must be washed in water by means of the application of ultrasonic generator means. After washing, the grains are put in a sterilizing bath and sterilized. The sterilized grains are then delivered to a sprouting apparatus for sprouting. After sprouting, the sprouted gains are delivered to the sterilizing apparatus and sterilized again. This grain sprouting and sterilizing procedure is complicated and takes much time.

SUMMARY OF THE INVENTION

The present invention has been accomplished under the circumstances in view. It is the main object of the present invention to provide an apparatus for sterilizing and sprouting grains, which enables grains to be sterilized and sprouted efficiently. The apparatus for sterilizing and sprouting grains comprises a container having a water inlet pipe, a water drain pipe, an overflow pipe, and a grains discharge control valve, a top cover covering the container and provided with ultraviolet lamps for sterilizing water in the container, a water supply coil connected to the water inlet pipe for guiding fresh water to the inside of the container, a disk-like or bowl-like wire gauze filter mounted in the container for carrying grains above the water supply coil, active carbon blocks mounted in the space between the water supply coil and the disk-like or bowl-like wire gauze filter, an ozone supply pipe adapted to supply ozone to water delivered to the inside of the container, and an ultrasonic generator adapted to generate ultrasonic waves in water in the container. Further, a temperature sensor is installed in the container, and adapted to control the temperature of water in the container.

DETAILED DESCRIPTION OF THE PREFERRED EMBODIMENT

Figure 1:
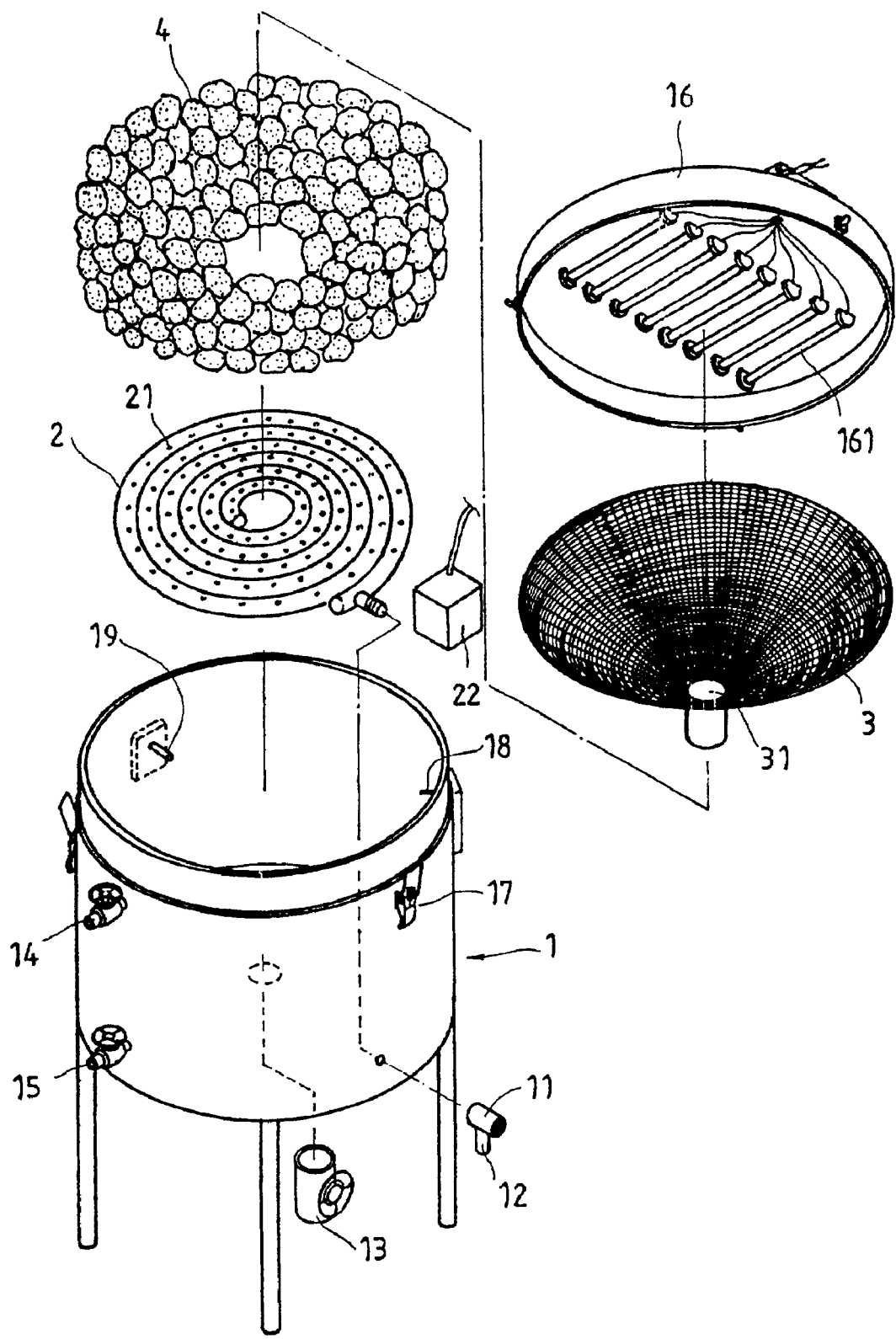
FIG. 1 is an exploded view of an apparatus for sterilizing and sprouting grains constructed according to the present invention.
Figure 2:
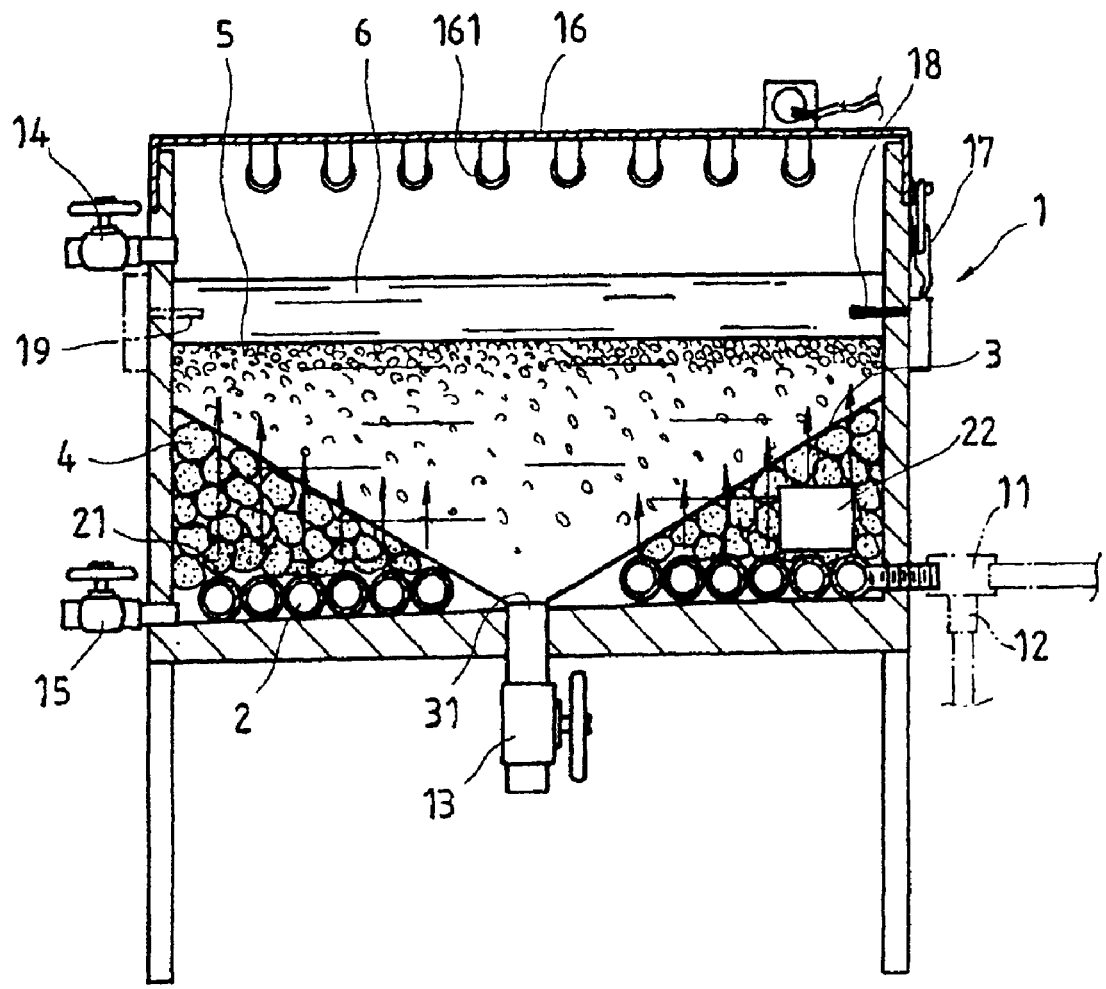
FIG. 2 is a sectional assembly view of the apparatus for sterilizing and sprouting grains according to the present invention.

Referring to FIGS. 1 and 2, an apparatus for sterilizing and sprouting grains in accordance with the present invention is shown comprising a container 1, a grains discharge control valve 13 provided at the bottom side of the container 1 and controlled to drain water from the container 1, a top cover 16 covering the top open side of the container 1, a water supply coil 2 spirally mounted in the container 1 at the bottom side, the water supply coil 2 having multiple water outlets 21, a disk-like or bowl-like wire gauze filter 3 mounted in the container 1 above the water supply coil 2, the disk-like or bowl-like wire gauze filter 3 having a bottom outlet pipe 31 connected to the grains discharge control valve 13, active carbon blocks 4 mounted in the container 1 and filled up the space between the water supply coil 2 and the bowl-like wire gauze filter 3, a plurality of ultraviolet lamp tubes 161 respectively mounted in the bottom side of the top cover 16, an emerged ultrasonic generator 22 mounted in the container 1 and embedded in the active carbon blocks 4, a water inlet pipe 11 mounted in the outside wall of the container 1 and connected to the water supply coil 2 and adapted to guide fresh water from an external water source to the water supply coil 2, an ozone supply pipe 12 connected to the water inlet pipe 11 and adapted to guide ozone from an external ozone generator (not shown) into fresh water passing through the water inlet pipe 11 to the water supply coil 2, an overflow pipe 14 installed in the container 1 near the top and adapted to guide an overflow of water out of the container 1, a drain pipe 15 installed in the periphery of the container 1 near the bottom and adapted to carry all water away from the container 1, a lock 17 provided at the container 1 and adapted to lock the top cover 16, an ozone sensor 18 installed in the container 1 and adapted to examine ozone concentration in water contained in the container 1, and a temperature sensor 19 installed in the container 1 and adapted to examine the temperature of water contained in the container 1.

Figure 3:
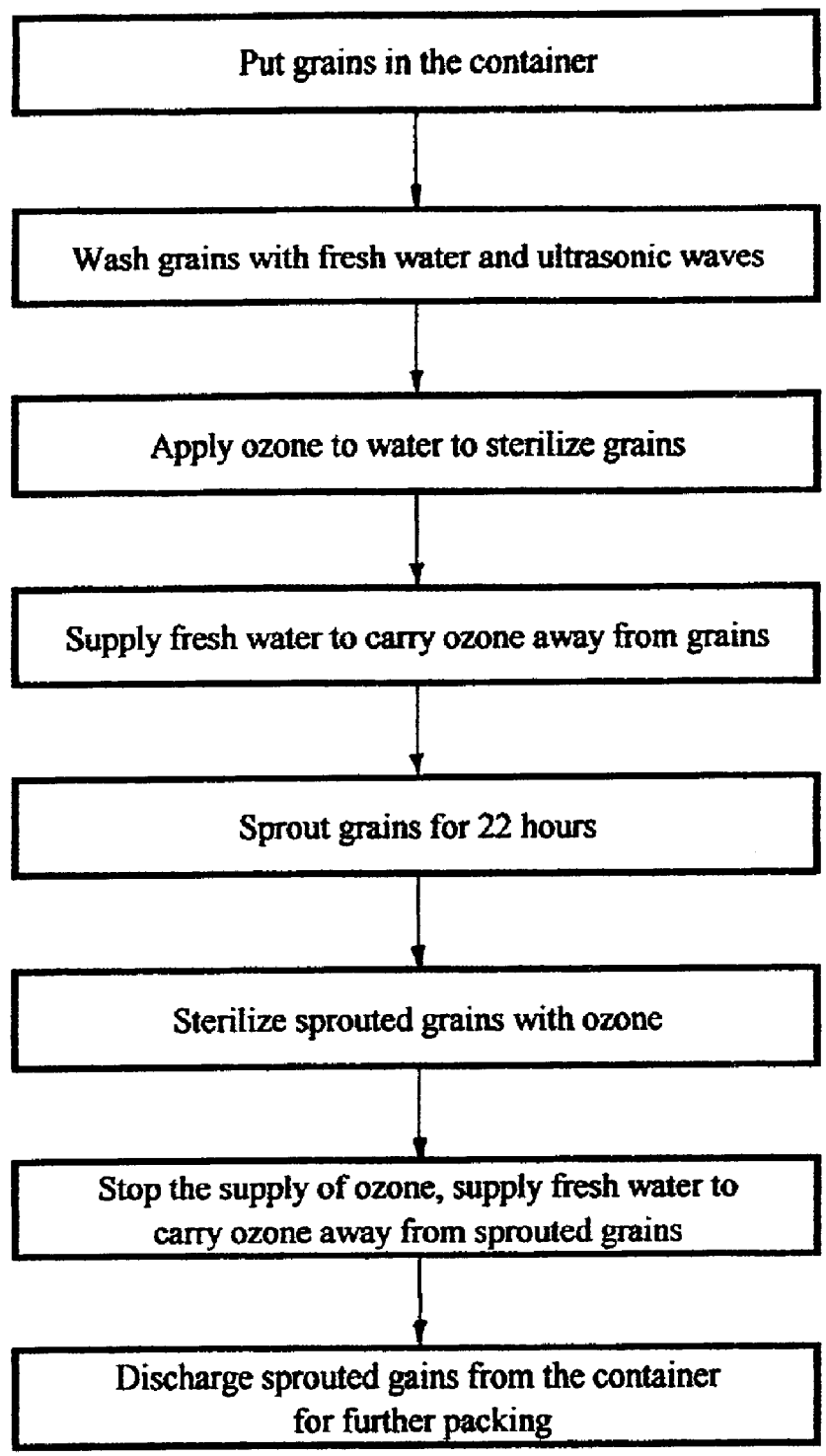
FIG. 3 is a block diagram explaining the operation of the present invention.

The operation of the present invention is outlined hereinafter with reference to FIG. 3. Materials, for example, grains are put in the container 1, and then fresh water 6 is delivered from the external water source through the water inlet pipe 1 and the water supply coil 2 into the container 1 and at the same time the ultrasonic generator 22 is started to generate ultrasonic waves to clean the grains, and then ozone is supplied to water 6 passing through the water inlet pipe 1 via the ozone supply pipe 12 to sterilize the grains for a predetermined length time, and then stop the supply of ozone during continuous supply of fresh water 6, which is controlled at the temperature of 38° C.~40° C. subject to the working of the temperature sensor 19, to the container 1, for enabling the grains to be sprouted within a length of time about 22 hours, and then ozone is supplied to fresh water 6 passing through the water inlet pipe 11 to sterilize the sprouts, and then the ozone supply pipe 12 is closed and fresh water 6 is continuously supplied to the container 1 to wash out ozone from the sprouts, and then water is carried away from the container 1 through the drain pipe 15, and then the grains discharge control valve 13 is opened to discharge sprouted grains. Further, during the process of sterilizing the grains, the ultraviolet lamp tubes 161 may be turned on to radiate water in the container 1.

While only one embodiment of the present invention has been shown and described, it will be understood that various modifications and changes could be made thereunto without departing from the spirit and scope of the invention disclosed.

What is claimed is:

1. An apparatus for sterilizing and sprouting grains comprising:

a container adapted to hold grains for sprouting, said container comprising an water inlet pipe adapted to guide fresh water from an external water source to the inside of said container, an overflow pipe adapted to guide an overflow of water out of said container, a grains discharge control valve disposed at a bottom side thereof and controlled to discharge sprouted grains out of said container;

a top cover covering said a top side of said container, said top cover comprising a plurality of ultraviolet lamps adapted to sterilize water contained in said container;

a water supply coil mounted inside said container and connected to said water inlet pipe, said water supply coil having a plurality of water outlets adapted to guide water from said water inlet pipe into the inside of said container;

a wire gauze filter mounted in said container above said water supply coil, said wire gauze filter having a bottom outlet pipe connected to said grains discharge control valve; and active carbon blocks mounted in said container and filled up the space between said water supply coil and said wire gauze filter.

2. The apparatus for sterilizing and sprouting grains as claimed in claim 1 further comprising a temperature sensor adapted to examine the temperature of water contained in said container.

3. The apparatus for sterilizing and sprouting grains as claimed in claim 1 further comprising a water drain pipe connected to said container and adapted to guide all water away from said container.

4. The apparatus for sterilizing and sprouting grains as claimed in claim 1 further comprising lock means provided at said container and adapted to lock said top cover.

5. The apparatus for sterilizing and sprouting grains as claimed in claim 1 further comprising ultrasonic generator means provided in said container and embedded in said active carbon blocks and adapted to generate ultrasonic waves.

6. The apparatus for sterilizing and sprouting grains as claimed in claim 1 further comprising an ozone supply pipe connected to said water inlet pipe and adapted to guide ozone from an external ozone supply source to water passing through said water inlet pipe to said water supply coil.

7. The apparatus for sterilizing and sprouting grains as claimed in claim 6 further comprising an ozone sensor mounted in said container and adapted to examine ozone concentration in water contained in said container.

\* \* \* \* \*